United States Patent

Abou-Gharbia

[11] Patent Number: 4,857,644
[45] Date of Patent: Aug. 15, 1989

[54] ARYL SULFONOPIPERAZINES AS ANTI-INFLAMMATORY AGENTS

[75] Inventor: Magid A. Abou-Gharbia, Wilmington, Del.

[73] Assignee: American Home Products Corporation, New York, N.Y.

[21] Appl. No.: 204,459

[22] Filed: Jun. 9, 1988

[51] Int. Cl.⁴ ............................................ G07D 241/04
[52] U.S. Cl. .................................... 544/295; 544/238; 544/360; 544/380; 544/382; 544/383; 544/398
[58] Field of Search ............... 544/295, 238, 360, 380, 544/382, 383, 398

[56] References Cited

U.S. PATENT DOCUMENTS 4,425,342 1/1984 Allen et al. ......................... 544/360
4,602,015 7/1986 Crisafulli et al. ..................... 544/295

FOREIGN PATENT DOCUMENTS 0061673 10/1982 European Pat. Off. .

Primary Examiner—Glennon H. Hollrah
Assistant Examiner—James H. Turnipseed
Attorney, Agent, or Firm—George Tarnowski

[57] ABSTRACT

There are disclosed compounds of the formula

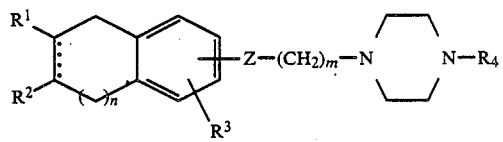

wherein
$R^1$ and $R^2$ are each, independently, hydrogen, lower alkyl or phenyl; or $R^1$ and $R^2$ taken together represent —$(CH_2)_4$— or

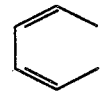

where the dotted line represents an optional double bond;
$R^3$ is hydrogen, lower alkyl, lower alkoxy or halo;
$R^4$ is pyridinyl, pyrimidinyl, pyrazinyl, benzyl, phenyl or phenyl substituted by lower alkyl, lower alkoxy, or halo;
Z is —$SO_2$— or

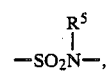

where $R^5$ is hydrogen or lower alkyl;
m is 0–4;
n is 0–2; and
the pharmaceutically acceptable salts thereof, and their use as anti-inflammatory agents.

6 Claims, No Drawings

ARYL SULFONOPIPERAZINES AS ANTI-INFLAMMATORY AGENTS

This invention relates to novel aryl sulfonopiperazines having anti-inflammatory activity.

According to the present invention there are provided compounds having the formula

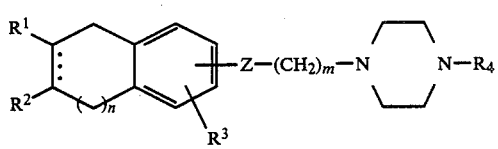

wherein
R$^1$ and R$^2$ are each, independently,, hydrogen, lower alkyl or phenyl; or R$^1$ and R$^2$ taken together represent —(CH$_2$)$_4$— or

where the dotted line represents an optional double bond;
R$^3$ is hydrogen, lower alkyl, lower alkoxy or halo;
R$^4$ is pyridinyl, pyrimidinyl, pyrazinyl, benzyl, phenyl or phenyl substituted by lower alkyl, lower alkoxy or halo;
Z is —SO$_2$— or

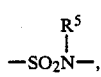

where R$^5$ is hydrogen or lower alkyl;
m is 0–4;
n is 0–2; and
the pharmaceutically acceptable salts thereof.

The terms "lower alkyl" and "lower alkoxy" refer to moieties having 1 to 6 carbon atoms in the carbon chain. The term "halo" refers to fluoro, chloro and bromo.

The compounds of the invention can be prepared by various synthetic routes using conventional methods. The most direct preparative route involves the reaction of a sulfonyl chloride intermediate with appropriately substituted piperazines to yield the desired final products:

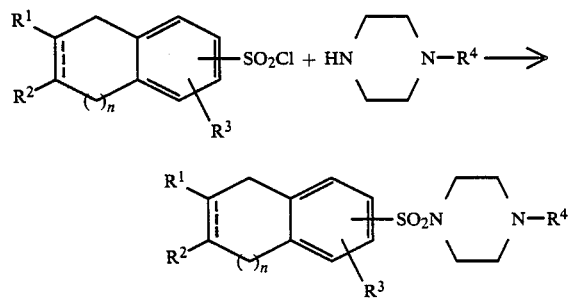

The above reaction, in which R$^1$, R$^2$, R$^3$ and R$^4$ are as defined hereinbefore, is carried out in an organic solvent such as methylene chloride, in the presence of triethylamine. The sulfonyl choride intermediates used in the above sequences can be readily prepared by reacting the desired precursor aryl starting material with chlorosulfonic acid in organic solvent, such as acetonitrile, as exemplified by the reaction of 5-methoxyindane with chlorosulfonic acid:

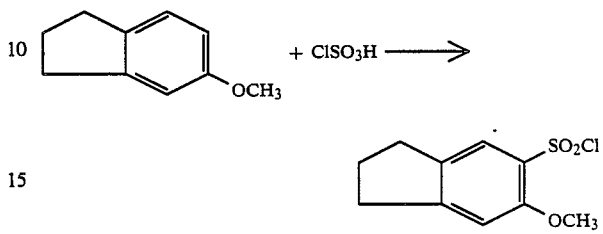

Compounds in which Z is

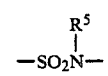

and m is 1–4, can be prepared according to the above described reaction sequence, using the sulfonyl chloride intermediate and an appropriately substituted piperazinylalkylamine:

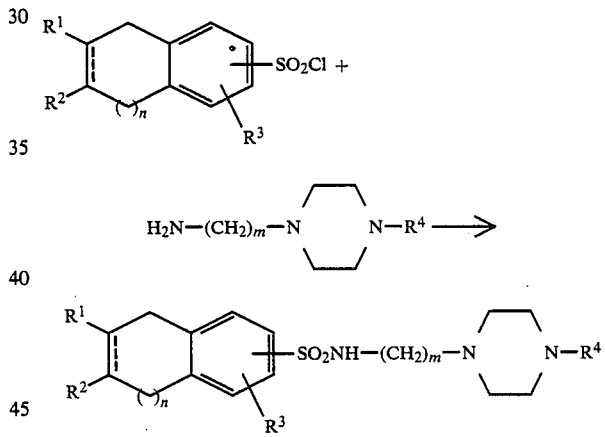

This reaction, in which R$^1$, R$^2$, R$^3$, R$^4$ and n are as defined hereinbefore, is also carried out in an organic solvent, such as methylene chloride and in the presence of triethylamine.

The starting materials used in the above-outlined preparative sequences are all avalable commercially or can be prepared by conventional methods disclosed in the chemical literature.

Compounds of the invention which contain a basic nitrogen are capable of forming pharmaceutically acceptable salts, including the salts of pharmaceutically acceptable organic and inorganic acids, such as hydrochloric, hydrobromic, sulfuric, nitric, phosphoric, methanesulfonic, benzenesulfonic, acetic, citric, pumaric, maleic, succinic and the like.

The compounds of the invention are anti-inflammatory agents and as such are useful in the treatment of such diseases as rheumatoid arthritis, osteoarthritis, tendinitis, bursitis, gout and similar conditions.

When the compounds of the invention are employed as anti-inflammatory agents, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The anti-inflammatory activity of the compounds of the invention may be demonstrated by a standard pharmacological procedure, which measures the in vivo activity of the compounds of the invention as anti-inflammatory agents in the rat carrageenan paw edema assay.

The following examples show the preparation and pharmacological testing of compounds within the invention.

EXAMPLE 1

1-(2-Pyrimidinyl-4-[(2,3-dihydro-6-methoxy-1H-indan-5-yl)sulfonyl]piperazine, hydrochloride hydrate A solution of 5-methoxyindane (10 g, 0.07 mol) is dissolved in 60 mL of acetonitrile and is added dropwise to a stirred chlorosulfonic acid solution while cooling over ½ hour. The clear solution turns thick green, the ice bath is removed and the solution is heated at 50°–60° C. for 3 hours. The resulting solution is poured into crushed ice and the grey gummy solid is extracted in methylene chloride (3×100 mL), dried over anhydrous $Na_2SO_4$ and the methylene chloride is removed under reduced pressure to afford 8 g of the crude sulfonyl chloride intermediate.

The title compound is prepared by adding to stirred solution of the above sulfonyl chloride intermediate (2.5 g, 0.01 mol) in 50 mL of methylene chloride, 1-(2-pyrimidinyl)piperazine dihydrochloride (2.5 g, 0.01 mol) and triethylamine (6 mL). The reaction mixture is stirred overnight and the methylene chloride solution is washed with water and dried over anhydrous $Na_2SO_4$. Evaporation of the methylene chloride under reduced pressure affords crude buff solid which is recrystallized from ethyl acetate; m.p. 111°–112° C. and is converted to the hydrochloride salt; m.p. 146°–148° C.

Analysis for: $C_{18}H_{22}N_4SO_3 \cdot HCl$
Calculated: C, 50.06; H, 5.70; N, 12.59.
Found: C, 50.40; H, 5.83; N, 13.06.

EXAMPLE 2

1-(9H-Fluoren-2-ylsulfonyl)-4-(phenylmethyl)piperazine, hydrochloride

A solution of 2-fluorene sulfonic acid potassium salt (20 g, 0.07 mol) and sulfonyl chloride (59.5 g, 0.5 mol) is stirred for 2 hours. The solvent is removed under reduced pressure and the residue is extracted with 3×100 mL methylene chloride. The methylene chloride extracts are collected, dried and evaporated to afford 18.5 g of the crude sulfonyl chloride intermediate.

The title compound is prepared by adding to a stirred solution of the above sulfonyl chloride intermediate (4 g, 0.015 mol) in 50 mL of methylene chloride (2.7 g, 0.015 mol), 1-(benzyl)piperazine (2.7 g, 0.015 mol) and triethylamine (6 mL). The reactin mixture is stirred overnight and the methylene chloride layer is washed with water and dried over anhydrous $Na_2SO_4$. Evaporation of the methylene chloride under reduced pressure affords crude product which is purified by HPLC using silica gel column and ethyl acetate as the eluent. The desired fractions ($R_f=0.8$) are evaporated to give pure free base which is converted to the hydrochloride salt; m.p. 274°–275° C. (33% yield).

Analysis for: $C_{24}H_{24}N_2SO_4 \cdot HCl$
Calculated: C, 65.38; H, 5.67; N, 6.36
Found: C, 65.68; H, 5.91; N, 6.0.

EXAMPLE 3

1-(3-Chlorophenyl)-4-(9H-fluoren-2-yl-sulfonyl)piperazine, hydrochloride

The title compound is prepared by adding to a stirred solution of 2-fluorenesulfonylchloride (4 g, 0.015 mol) in 50 mL of methylene chloride, 1-(3-chlorophenyl)piperazine (3 g, 0.013 mol) and triethylamine (6 mL). The solution is stirred overnight and the methylene chloride layer is washed with water and dried over anhydrous $Na_2SO_4$. Evaporation of the methylene chloride under reduced pressure affords crude product which is purified as in Example 2 and converted to the hydrochloride salt; m.p. 219°–221° C. (35% yield).

Analysis for: $C_{23}H_{21}N_2ClSO_2 \cdot HCl$
Calculated: C, 59.86; H, 4.77; N, 6.07
Found: C, 59.62; H, 4.92; N, 6.11.

EXAMPLE 4

2-[4-(2-Pyrimidinyl)-1-piperazinyl]-1-[2,3-dihydro-6-methoxy-1H-indan-5-yl]ethyl sulfonamide, dihydrochloride, hemihydrate To a stirred solution of 5-chlorosulfonyl-6-methoxyindane (2.51 g, 0.010 mol) and 4-[(2-pyrimidinyl-1-piperazinyl]ethylamine (2.23 g, 0.01 mol) in methylene chloride (55 mL) is added triethylamine (7.5 mL, 5.4 g, 0.054 mol) in one portion at room temperature. Stirring is continued for 48 hours and the methylene chloride solution is washed with water, dried over anhydrous $Na_2SO_4$ and evaporated under reduced pressure. The crude product is purified by HPLC giving 2.1 g (50% yield) of the title compound, which is converted to the dihydrochloride salt; m.p. 162°–165° C.

Analysis for: $C_{20}H_{27}N_5O_3S \cdot 2HCl \cdot \frac{1}{2}H_2O$
Calculated: C, 48.09; H, 6.05; N, 14.02

Found: C, 47.79; H, 5.94; N, 13.90.

EXAMPLE 5

3-[4-(2-Methoxyphenyl)-1-piperazinyl]-1-[2,3-dihydro-6-methoxy-1H-indan-5-yl]propylsulfonamide, dihydrochloride The title compound is prepared following the procedure of Example 1 using 4-[(2-methoxyphenyl)-1-piperazinyl)propylamine instead of 1-(2-pyrimidinyl)-piperazine and is converted to the dihydrochloride salt; m.p. 197°–201° C.

Analysis for: $C_{23}H_{31}N_2O_4S \cdot 2HCl$
Calculated: C, 54.13; H, 6.63; N, 7.89
Found: C, 54.09; H, 6.66; N, 7.87.

EXAMPLE 6

The compounds of the invention are tested in the rat carrageenan paw edema assay to determine their ability to inhibit the acute inflammatory response.

This assay is carried out as follows:

140–180 mg male Sprague-Dawley rats, in groups of 6 animals are injected subcutaneously in the right paw with 0.1 ml of 1% carrageenan at zero time. Mercury plethysmographic readings (ml) of the paw are made at zero time and 3 hours later. Test compounds are suspended or dissolved in 0.5% methylcellulose and given perorally 1 hour prior to carrageenan administration.

The increase in paw volume (edema in ml.) produced by the carrageenan is measured. Paw edema is calculated (3 hour volume minus zero time volume), and percent inhibition is determined. Unpaired Student's t-test is used to determine statistical significance.

When tested in this assay, the compounds of the invention gave the following results:

TABLE 1

| Compound of Example No. | % Inhibition at 50 mg/kg(peroral) |
| --- | --- |
| 1 | 55 |
| 2 | 26 |
| 3 | 22 |

The results show that the componds tested have oral activity in the rat carrageenan paw edema assay, evidencing an effect on the acute inflammatory response.

What is claimed is:

1. A compound having the formula:

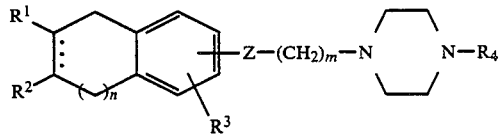

wherein
$R^1$ and $R^2$ are each, independently, hydrogen, lower alkyl or phenyl; or $R^1$ and $R^2$ taken together represent —$(CH_2)_4$— or

where the dotted line represents an optional double bond;
$R^3$ is hydrogen, lower alkyl, lower alkoxy or halo;
$R^4$ is pyridinyl, pyrimidinyl, pyrazinyl, benzyl, phenyl or phenyl substituted by lower alkyl, lower alkoxy or halo;
Z is —$SO_2$— or

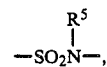

where $R^5$ is hydrogen or lower alkyl;
m is 0–4;
n is 0–2; and
the pharmaceutically acceptable salts thereof.

2. The compound of claim 1, having the name 1-(2-pyrimidinyl-4-[(2,3-dihydro-6-methoxy-1H-indan-5-yl)sulfonyl]piperazine, hydrochloride hydrate.

3. The compound of claim 1, having the name 1-(9H-fluoren-2-ylsulfonyl)-4-(phenylmethyl)piperazine, hydrochloride.

4. The compound of claim 1, having the name 1-(3-chlorophenyl)-4-(9H-fluoren-2-ylsulfonyl)piperazine, hydrochloride.

5. The compound of claim 1, having the name 2-[4-(2-pyrimidinyl)-1-piperazinyl]-1-[2,3-dihydro-6-methoxy-1H-indan-5-yl]ethyl sulfonamide, dihydrochloride, hemihydrate.

6. The compound of claim 1, having the name 3-[4-(2-methoxyphenyl)-1-piperazinyl]-1-[2,3-dihydro-6-methoxy-1H-indan-5-yl]propylsulfonamide, dihydrochloride.

* * * * *